United States Patent [19]
Fukaya et al.

[11] Patent Number: 5,914,257
[45] Date of Patent: Jun. 22, 1999

[54] STRUCTURAL GENE FOR MEMBRANE-BOUND ALDEHYDE DEHYDROGENASE

[75] Inventors: Masahiro Fukaya; Kenji Tayama; Toshimi Tamaki, all of Aichi-ken; Haruko Izumo, Shizuoka-ken; Hajime Okumura; Yoshiya Kawamura, both of Aichi-ken, all of Japan

[73] Assignee: Nakano Vinegar Co., Ltd., Aichi-ken, Japan

[21] Appl. No.: 07/987,260

[22] Filed: Dec. 7, 1992

Related U.S. Application Data

[63] Continuation of application No. 07/856,834, Mar. 23, 1992, abandoned, which is a continuation of application No. 07/318,279, Mar. 3, 1989, abandoned.

[30] Foreign Application Priority Data

| Mar. 8, 1988 | [JP] | Japan | ................................. 63-52709 |
| Feb. 15, 1989 | [JP] | Japan | ................................. 1-33775 |

[51] Int. Cl.$^6$ .............................. C12N 9/04; C12N 15/53; C12P 7/54
[52] U.S. Cl. .................... 435/190; 435/140; 435/320.1; 435/252.3; 435/252.33; 536/23.2
[58] Field of Search .................... 435/190, 140, 435/172.3, 320.1, 252.3, 252.33; 536/23.2

[56] References Cited

PUBLICATIONS

Agric. Biol. Chem., "Purification and Characterization of Membrane–Bound Aldehyde Dehydrogenase From *Gluconobacter Suboxydans*", O. Adachi et al., vol. 44, No. 3, 1980, pp. 503–515.

Agric. Biol. Chem., "Purification and Characterization of Aldehyde Dehydrogenase of *Acetobacter Aceti*", M. Ameyama et al., vol. 45, No. 8, 1981, pp. 1889–1890.

Chemical Abstracts, "Cloning of the Membrane–Bound Aldehyde Dehydrogenase Gene of Acetobacter Polyoxogenes and Improvement of Acetic Acid Production by Use of the Cloned Gene", M. Fukaya et al., vol. 110, No. 15, Apr. 10th 1989, p. 207, 129805k and Appl. Environ. Microbiol, 1989, 55(1), 171–6.

Van Vunakis—Immunochemical Techniques Part B—Methods in Enzymology, vol. 73 (1981).

Hanahan, D.—Techniques for Transformation of *E. coli*—DNA Cloning vol. 1—Chapter 6 (1985).

Wang, et al.—Screening Expression Libraries with Nonradioactive Immunological Probes—Gene, 37:267–269 (1985).

Davis, et al.—Advanced Bacterial Genetics—A Manual for Genetic Engineering (1980).

Birnboim, et al.—A Rapid Alkaline Extraction Procedure for Screening Recombinant Plasmid DNA—Nucleic Acids Research—vol. 7, No. 6 (1979).

Burnette—"Western Blotting": Electrophoretic Transfer of Proteins from Sodium Dodecyl Sulfate–Polyaceylamide Gels to Unmodified Nitrocellulose and Radiographic Detection with Antibody and Radioiodinated Protein A—Analytical Biochemistry 112:95–203 (1981).

Southern—Detection of Specific Sequences Among DNA Fragments Separated by Gel Electrophoresis—J. Mol. Biol. 98:503–507 (1975).

Hohn, et al.—A Small Cosmid for Efficient Cloning of Large DNA Fragments—Gene 11:291–298 (1980).

Fukaya, et al.—Improved Transformation Method of Acetobacter with Plasmid DNA—Agric. Biol. Chem. 49(7):2091–2097 (1985).

Messing—New M13 Vectors for Cloning—Methods in Enzymology, vol. 101, Recombinant DNA, Part C (1983).

Suggs et al. "Use of synthetic digonucleotides as hybridization probes". . . *PNAS USA* vol. 78, #11 pp. 6613–6617 1981.

Fukaya et al. "Construction of New Shuttle Vectors for Acetobacter" *Agric. Biol Chem* 49(7) 2083–90 1985.

Fukaya et al "Develop. of Host–Vector System for *Gluconobacter suboxydans*". *Agric. Biol Chem* 49(8) 2407–11 1985.

Okumura, H. et al., Biochemical Characteristics of Spontaneous Mutants of *Acetobacter aceti* Deficient in Ethanol Oxidation, Agric. Biol. Chem. 49(8):2485–2487 (1985).

Okumura, et. al.—Biochemical Characteristics of Spontaneous Mutants of Acetobacter aceti Deficient in Ethanol Oxidation—Agric. Biol. Chem. 49(8):2485–2487 (1987).

Okumura, et al.—Biochemical Characteristics of Spontaneous Mutants of *Acetobacter aceti* Deficient in Ethanol Oxidation—Bgric. Biol. Chem. 49(8):2485–2487 (1987).

*Primary Examiner*—Keith D. Hendricks
*Attorney, Agent, or Firm*—Browdy and Neimark

[57] ABSTRACT

This invention relates to the structural gene for the membrane-bound aldehyde dehydrogenase derived from microorganisms belonging to the genus Acetobacter, said structural gene having a molecular size of about 3.6 Kb and having a restriction enzyme cleavage map as shown in FIG. 1; to a plasmid containing said structural gene; to an acetic acid bacterium transformed by said plasmid; and to an acetic acid fermentation process using said transformant.

13 Claims, 9 Drawing Sheets

```
1
ATG.GGT.AGA.TTA.AAC.CGC.TTC.CGC.CTT.GGC.AAG.GAC.GGG.CGC.CGT.GAA.CAG.GCT.TCC.CTG
MET-Gly-Arg-Leu-Asn-Arg-Phe-Arg-Leu-Gly-Lys-Asp-Gly-Arg-Arg-Glu-Gln-Ala-Ser-Leu

61
TCA.CGT.CGC.GGC.TTC.CTT.GTC.ACC.TCC.CTT.GGC.GCC.GGC.GTC.ATG.TTT.GGC.TTC.GCG.CGT
Ser-Arg-Arg-Gly-Phe-Leu-Val-Thr-Ser-Leu-Gly-Ala-Gly-Val-MET-Phe-Gly-Phe-Ala-Arg

121
CCT.TCA.TCC.GCC.AAC.CAG.ATT.TTC.CCG.CTC.GAC.CGG.TCG.CCG.GGT.GAC.GGG.GCG.TTC
Pro-Ser-Ser-Ala-Asn-Gln-Ile-Phe-Pro-Leu-Asp-Arg-Ser-Leu-Pro-Gly-Asp-Gly-Ala-Phe

181
GAA.CCC.ACC.ATC.TGG.TGT.TCG.ATC.GCA.CCC.GAT.GGG.GAA.ATC.ACG.GTC.AAC.ATC.ATC.CGC
Glu-Pro-Thr-Ile-Trp-Cys-Ser-Ile-Ala-Pro-Asp-Gly-Glu-Ile-Thr-Val-Asn-Ile-Ile-Arg

241
GCG.GAA.ATG.GGC.CAG.CAT.ATC.GGC.ACC.GCC.CTT.GCC.CGC.ATC.ATC.GCG.GAT.GAA.ATG.GAA
Ala-Glu-MET-Gly-Gln-His-Ile-Gly-Thr-Ala-Leu-Ala-Arg-Ile-Ile-Ala-Asp-Glu-MET-Glu

301
GCC.GAC.TGG.AGC.AAG.GTC.CGC.ATC.AAC.TAC.GTG.GAC.ACC.GAC.CCC.AAA.TGG.GGG.CTG.ATG
Ala-Asp-Trp-Ser-Lys-Val-Arg-Ile-Asn-Tyr-Val-Asp-Thr-Asp-Pro-Lys-Trp-Gly-Leu-MET
```

FIG. 3B

361
GTT.ACC.GGT.GGC.AGC.TGG.TCG.GTG.TGG.ATG.ACA.TGG.GAC.GTC.TTC.CGC.CAG.GCT.GGC.GCC
Val-Thr-Gly-Ser-Trp-Ser-Val-Trp-MET-Thr-Trp-Asp-Val-Phe-Arg-Gln-Ala-Gly-Ala

421
GCG.ACG.CGC.ACG.GCC.ATG.GTC.GAG.GAA.GGC.GCC.CGC.CTG.CTG.GGC.ACC.ACG.CCG.GAC.AAG
Ala-Thr-Arg-Thr-Ala-MET-Val-Glu-Gly-Ala-Arg-Leu-Leu-Gly-Thr-Thr-Pro-Asp-Lys

481
TGC.ACG.GTC.GCC.AGC.AGC.ATC.GTC.AGT.GCC.GGT.GGC.AAG.CAG.ATC.AGC.TTT.GGC.GAC.ATC
Cys-Thr-Val-Ala-Ser-Ser-Ile-Val-Ser-Ala-Gly-Gly-Lys-Gln-Ile-Ser-Phe-Gly-Asp-Ile

541
GTG.GCC.AAG.GGG.CAT.CCG.TCC.CAT.GCC.TTC.ACG.CCC.GAG.GAA.ATG.GCC.AAG.CTG.CCG.CTC
Val-Ala-Lys-Gly-His-Pro-Ser-His-Ala-Phe-Thr-Pro-Glu-Glu-MET-Ala-Lys-Leu-Pro-Leu

601
AAG.CCC.GCC.AGC.GAA.CGC.AGG.CTG.ATC.GGC.AAT.GCC.GAA.CTC.AAG.GCG.CTG.GAC.ATT.CCG
Lys-Pro-Ala-Ser-Glu-Arg-Arg-Leu-Ile-Gly-Asn-Ala-Glu-Leu-Lys-Ala-Leu-Asp-Ile-Pro

661
GCC.AAG.ACC.AAC.GGC.ACG.GCC.ATC.TAT.GGC.ATC.GAC.GCC.AAG.GTG.GAA.GGC.ATG.CTG.TAC
Ala-Lys-Thr-Asn-Gly-Thr-Ala-Ile-Tyr-Gly-Ile-Asp-Ala-Lys-Val-Glu-Gly-MET-Leu-Tyr

FIG. 3C

```
721
GGC.CGC.CCC.AAG.ATG.CCG.CCG.ACG.CGC.TCC.AAG.GTC.CGT.TCG.GTT.GAC.GAT.ACC
Gly-Arg-Pro-Lys-MET-Pro-Pro-Thr-Arg-Tyr-Gly-Ser-Lys-Val-Arg-Ser-Val-Asp-Asp-Thr

781
GAG.GCC.AAG.AAG.ATC.AAG.GGC.TAT.GTC.CGC.TAC.CTG.CTG.ATC.GAT.GAT.CCG.TCG.CAG.GTC
Glu-Ala-Lys-Lys-Ile-Lys-Gly-Tyr-Val-Arg-Tyr-Leu-Leu-Ile-Asp-Asp-Pro-Ser-Gln-Val

841
GTG.CAG.GGC.TGG.GTC.GTG.GTG.CTG.GCG.GAA.AGC.TAC.AGC.GCC.ATC.CGC.GCG.ACC.GAT
Val-Gln-Gly-Trp-Val-Val-Val-Leu-Ala-Glu-Ser-Tyr-Ser-Ala-Ala-Ile-Arg-Ala-Thr-Asp

901
GCG.CTG.AAG.GTT.GAA.TGG.ACG.CCG.GGT.GAG.ACG.ATC.CAC.ACG.TCC.GAA.CGC.GAC.ATT.CAG
Ala-Leu-Lys-Val-Glu-Trp-Thr-Pro-Gly-Glu-Thr-Ile-His-Thr-Ser-Glu-Arg-Asp-Ile-Gln

961
GAC.CGT.GGC.CGC.GAA.CTG.ATC.AAC.AAC.AAG.GCA.GGC.GGC.GTC.TAC.ATC.TTC.AAT.GAT.GAT
Asp-Arg-Gly-Arg-Glu-Leu-Ile-Asn-Asn-Lys-Ala-Gly-Gly-Val-Tyr-Ile-Phe-Asn-Asp-Asp

1021
GGC.GTG.GAC.CAG.GCC.TTT.GGC.AGT.GCG.CAT.ACG.GTC.ATG.GAT.CAG.GAA.TAT.ACC.TGT.GCA
Gly-Val-Asp-Gln-Ala-Phe-Gly-Ser-Ala-His-Thr-Val-MET-Asp-Gln-Glu-Tyr-Thr-Cys-Ala
```

FIG. 3D

```
1081
TCC.GTG.CTG.CAT.TAC.CAG.CTG.GAA.CCG.ACC.AAC.GCG.CTG.GCC.TTT.GAA.AAG.GAC.GGT.GTT
Ser-Val-Leu-His-Tyr-Gln-Leu-Glu-Pro-Thr-Asn-Ala-Leu-Ala-Phe-Glu-Lys-Asp-Gly-Val

1141
TAC.GAA.ATC.CAC.GCG.GGT.AAC.CAG.TGG.CAG.AGC.CTG.ATC.CTG.CCC.ACG.CTG.GCC.AAG.TCG
Tyr-Glu-Ile-His-Ala-Gly-Asn-Gln-Trp-Gln-Ser-Leu-Ile-Leu-Pro-Thr-Leu-Ala-Lys-Ser

1201
CTG.CAG.GTG.CCT.GAA.AGC.AAG.GTC.ATC.CTG.CGC.AGC.TAC.CTG.CTG.GGT.GGC.GGG.TTT.GGC
Leu-Gln-Val-Pro-Glu-Ser-Lys-Val-Ile-Leu-Arg-Ser-Tyr-Leu-Leu-Gly-Gly-Gly-Phe-Gly

1261
CGC.CGG.CTG.AAC.GGG.GAT.TAC.ATG.ATC.CCG.GCC.GCC.CTT.GCG.TCC.AAG.GCG.CTG.GGC.GGC
Arg-Arg-Leu-Asn-Gly-Asp-Tyr-MET-Ile-Pro-Ala-Ala-Leu-Ala-Ser-Lys-Ala-Leu-Gly-Gly

1321
AAG.CCG.GTC.AAG.CTG.ATC.CTG.ACG.CGG.TCG.GAT.GAC.ATG.CAG.TTC.GAT.TCC.TTC.CGC.TCG
Lys-Pro-Val-Lys-Leu-Ile-Leu-Thr-Arg-Ser-Asp-Asp-MET-Gln-Phe-Asp-Ser-Phe-Arg-Ser

1381
CCT.TCG.GTC.CAG.CGT.GTC.CGC.ATG.GCG.TTC.GAC.GCC.AGC.GAC.AGG.ATC.ACC.GCC.ATG.GAT
Pro-Ser-Val-Gln-Arg-Val-Arg-MET-Ala-Phe-Asp-Ala-Ser-Asp-Arg-Ile-Thr-Ala-MET-Asp
```

FIG. 3E

```
1441
TAC.CAG.GCC.GCT.GCG.GGC.TGG.CCC.ACG.GGC.GTG.ATG.GCC.GAA.GCG.TTT.ATG.GAA.AAG.GGC
Tyr-Gln-Ala-Ala-Gly-Trp-Pro-Thr-Gly-Val-MET-Ala-Glu-Ala-Phe-MET-Glu-Lys-Gly

1501
GTG.GAT.GGC.AAG.CCG.TAT.GAC.CAG.TTC.GCC.ATC.GCT.GGT.GGC.GAC.CAC.TGG.TAC.GAA.GTC
Val-Asp-Gly-Lys-Pro-Tyr-Asp-Gln-Phe-Ala-Ile-Ala-Gly-Gly-Asp-His-Trp-Tyr-Glu-Val

1561
GGT.GCC.TTC.CGG.GTG.CGT.GCG.CTG.CGT.AAT.GAC.CTG.GCG.GAA.AAG.ACA.TTC.CGT.CCC.GGC
Gly-Ala-Phe-Arg-Val-Arg-Ala-Leu-Arg-Asn-Asp-Leu-Ala-Glu-Lys-Thr-Phe-Arg-Pro-Gly

1621
TGG.CTG.CGT.TCG.GTC.AGC.CCC.GGC.TGG.ACC.AGC.TGG.GGG.GTC.GAG.TGC.TTC.CTT.GAT.GAA
Trp-Leu-Arg-Ser-Val-Ser-Pro-Gly-Trp-Thr-Ser-Trp-Gly-Val-Glu-Cys-Phe-Leu-Asp-Glu

1681
GTC.GCG.CAC.CGC.CAG.AAG.AAG.GAT.CCT.GCG.CAG.TTC.CGT.CTT.GAA.CTG.TTG.ACC.GGG.CAG
Val-Ala-His-Arg-Gln-Lys-Lys-Asp-Pro-Ala-Gln-Phe-Arg-Leu-Glu-Leu-Leu-Thr-Gly-Gln

1741
GGC.CGT.AAC.AAG.GGG.CAG.GCG.CCC.GAT.TCC.GTC.GGT.GGC.GCG.CTG.CGT.CAG.GCC.GCT.GTC
Gly-Arg-Asn-Lys-Gly-Gln-Ala-Pro-Asp-Ser-Val-Gly-Gly-Ala-Leu-Arg-Gln-Ala-Ala-Val
```

FIG. 3F

```
1801
GTG.CGC.AGG.CTT.ATG.GAA.AAG.GTG.AAC.TGG.GGC.AAG.ACC.AGC.CTG.CCC.AAG.GAC.ACC.GCG
Val-Arg-Arg-Leu-MET-Glu-Lys-Val-Asn-Trp-Gly-Lys-Thr-Ser-Leu-Pro-Lys-Asp-Thr-Ala

1861
ATG.GGC.CTT.GCC.ACC.ACG.GCG.GGG.CAG.GAA.CGC.GGC.ATG.CCG.ACG.TGG.GAT.CGG.TGT.GTG
MET-Gly-Leu-Ala-Thr-Thr-Ala-Gly-Gln-Glu-Arg-Gly-MET-Pro-Thr-Trp-Asp-Arg-Cys-Val

1921
GCG.CAG.GTG.CAT.GTG.GAC.CGC.AGC.ACG.GGC.GTC.GTG.ACA.TGC.CAG.AAG.CTG.ACC.ATC.CTG
Ala-Gln-Val-His-Val-Asp-Arg-Ser-Thr-Gly-Val-Val-Thr-Cys-Gln-Lys-Leu-Thr-Ile-Leu

1981
GTC.GAT.GCG.GGT.ACC.GTG.GTT.GAC.CCC.GAT.GGC.GCG.AAG.GCC.CAG.ACC.GAG.GGT.GCT.GCG
Val-Asp-Ala-Gly-Thr-Val-Val-Asp-Pro-Asp-Gly-Ala-Lys-Ala-Gln-Thr-Glu-Gly-Ala-Ala

2041
CTG.TGG.GGC.CTG.AGC.ATG.GTC.CTG.TTC.GAG.AAC.ACG.GAA.ATC.GTC.AAC.GGC.ATG.CCG.GTT
Leu-Trp-Gly-Leu-Ser-MET-Val-Leu-Phe-Glu-Asn-Thr-Glu-Ile-Val-Asn-Gly-MET-Pro-Val

2101
GAC.CGT.AAC.CTG.AAC.ACC.TAT.ACG.CCA.CTG.CGT.ATT.GCC.GAC.ACG.CCG.GAA.ATG.GAC.ATC
Asp-Arg-Asn-Leu-Asn-Thr-Tyr-Thr-Pro-Leu-Arg-Ile-Ala-Asp-Thr-Pro-Glu-MET-Asp-Ile
```

FIG. 3G

```
2161
GAG.TTC.CTG.CCC.AGC.ACC.GAA.AAG.CCG.ATG.GGT.CTG.GGT.GAA.CCG.GGC.ACG.ACG.GTG.GTC
Glu-Phe-Leu-Pro-Ser-Thr-Glu-Lys-Pro-MET-Gly-Leu-Gly-Glu-Pro-Gly-Thr-Thr-Val-Val

2221
GGT.CCT.GCA.ATC.GGC.AAC.GCC.ATA.TTC.AAT.GCC.GTG.GGT.GTC.CGC.CTG.CGT.CAT.ATG.CCG
Gly-Pro-Ala-Ile-Gly-Asn-Ala-Ile-Phe-Asn-Ala-Val-Gly-Val-Arg-Leu-Arg-His-MET-Pro

2281
GTC.CGT.CCG.GCG.GAT.GTG.CTG.CGC.GGC.CTG.CAG.AAC.GGC
Val-Arg-Pro-Ala-Asp-Val-Leu-Arg-Gly-Leu-Gln-Asn-Gly
```

STRUCTURAL GENE FOR MEMBRANE-BOUND ALDEHYDE DEHYDROGENASE

This application is a continuation of application Ser. No. 07/856,834, filed Mar. 23, 1992, now abandoned, which is a continuation of application Ser. No. 07/318,279, filed Mar. 3, 1989, now abandoned.

FIELD OF THE INVENTION

This invention relates to the structural gene for the membrane-bound aldehyde dehydrogenase derived from microorganisms belonging to the genus Acetobacter, to a plasmid containing the same, and to the use of said plasmid.

The membrane-bound aldehyde dehydrogenase produced by microorganisms belonging to the genus Acetobacter is an enzyme that oxidizes an aldehyde into the corresponding acid by the aid of pyrrolo-quinoline quinone as prosthetic group. This is an enzyme of high industrial value which participates in the oxidation of ethanol into acetic acid in acetic acid fermentation, and is used for the quantitative analysis of various aldehydes and for the oxidative decomposition of aldehydes responsible for disagreeable odor of foods.

This invention also benefits the field of acetic acid fermentation because acetic acid bacteria producing said enzyme in larger quantities inside the cells ensure higher rate of acetic acid fermentation, thereby enhancing the productivity of acetic acid.

PRIOR ART AND PROBLEMS INVOLVED THEREIN

The membrane-bound aldehyde dehydrogenase has been produced by growing a microorganism belonging to the genus Acetobacter or Gluconobacter, and used in the form of untreated microbial cells thus grown or as a pure product after extraction from the cells [Agricultural and Biological Chemistry, 44, 503 (1980); ibid., 45, 1889 (1981)].

This enzyme, however, is contained in the microbial cells in small amounts, and is so unstable that it tends to be inactivated during the extraction and purification steps and cannot be isolated with a sufficiently high yield. Hence, it is difficult to obtain this enzyme in large quantities. It would be possible to create mutants that contain this enzyme in larger amounts, but there is no report as yet on a mutant capable of producing this enzyme in a sufficiently large quantity inside the cells.

BRIEF DESCRIPTION OF THE DRAWINGS

The abbreviations in the amino acid sequence have the meanings as listed below.

| | |
|---|---|
| MET: Methionine | Ala: Alanine |
| Arg: Arginine | Asn: Asparagine |
| Asp: Aspartic acid | Cys: Cystein |
| Gln: Glutamine | Glu: Glutamic acid |
| Gly: Glycine | His: Histidine |
| Ile: Isoleucine | Leu: Leucine |
| Lys: Lysine | Phe: Phenylalanine |
| Pro: Proline | Ser: Serine |
| Thr: Threonine | Trp: Tryptophan |
| Tyr: Tyrosine | Val: Valine |

MEANS TO SOLVE THE PROBLEMS

As a result of intensive studies to solve the above problems by DNA recombination techniques, we have succeeded in isolating the membrane-bound aldehyde dehydrogenase gene and introducing it into a plasmid, and have found that use of this plasmid with said structural gene introduced therein increases the content of said enzyme inside the cells, thereby enhancing the efficiency of acetic acid fermentation. This invention was accomplished on the basis of these findings.

Thus, this invention relates to a plasmid containing the structural gene for the membrane-bound aldehyde dehydrogenase derived from microorganisms of Acetobacter and having a molecular size of about 3.6 Kb; to a microorganism of Acetobacter or Gluconobacter transformed by said plasmid; and to an acetic acid fermentation process using said transformant.

The membrane-bound aldehyde dehydrogenase of this invention (hereinafter abbreviated as "ALDH") is an enzyme (a protein having a molecular weight of about 75,000) which is the key substance for the activity exhibited by the novel aldehyde dehydrogenase complex disclosed in Japanese Patent Kokai No.12279 (1988). It is produced by a group of Acetobacter microorganisms typified by Acetobacter altoacetigenes MH-24 strain (FERM BP-491). A DNA fragment containing the structural gene for said enzyme can be isolated from the total DNA harbored by a microorganism of Acetobacter capable of producing said enzyme. The total DNA may be prepared, for example, by the method disclosed in Japanese Patent Kokai No.9489 (1985). From this total DNA, can be isolated the DNA fragment containing the ALDH structural gene according to the procedure described in EXAMPLE 1—by preparing the antibody against said enzyme and screening out a clone containing the objective gene through the antigen-antibody reaction.

The said enzyme can be prepared according to the method disclosed in Japanese Patent Kokai No.12279 (1988)—by separating the purified aldehyde dehydrogenase complex into two subunits through electrophoresis on SDS-polyacrylamide gel, extracting the protein having a molecular weight of 75,000 from the gel, and using this protein as antigen. The antibody against ALDH can be obtained, for example, by the method described in "Methods in Enzymology", 73, 46 (1981); immunization repeated twice at an interval of about two weeks forms an antibody specific to ALDH after 1 to 1.5 months. The antibody thus formed may be isolated as a crude product by subjecting the immunized serum to ammonium sulfate fractionation, which can be further purified by ion-exchange chromatography. When the antibody is used for isolation of the objective gene, the immunized serum containing the same may be employed after proper dilution.

On the other hand, the total DNA is cleaved with a suitable restriction enzyme, the resulting fragment is ligated, by the aid of T4 DNA ligase, with an expression vector plasmid previously cleaved with a proper restriction enzyme, and the ligated product is used for transforming a strain of *Escherichia coli*. As the expression vector, may be used a vector plasmid which carries the promoter and operater for β-galactosidase gene and allows gene expression induced by isopropyl-β-thiogalactopyranoside (for example, pUC18).

Any known techniques may be used for the transformation of *Escherichia coli*, but it is preferable to adopt a method with high efficiency for gene introduction, for example, the method described in "DNA Cloning", Vol. 1, p109, IRL Press (1985). The strain containing the intended gene can be screened out from the transformants thus produced according, for example, to the method described in "Gene", 37, 267 (1985); allowing the cell debris of the transformants to react with the antibody, and detecting the strain showing specific reactivity. The strain thus selected contains the total length of the intended gene in some cases, but only a part of the gene in other cases.

When the strain contains only a part of the intended gene, the total gene can be obtained by the Southern hybridization technique using the part of gene as probe and isolating a fragment homologous to the probe.

In order to be used for the production of ALDH, the DNA fragment containing the ALDH structural gene thus isolated must be coupled with a gene having promoter activity to function in host cells. As the promoter to ensure the formation of ALDH protein in a microorganism of Acetobacter or Gluconobacter, may be used, in addition to the one inherent to the ALDH gene, a different gene derived from acetic acid bacteria and having promoter activity, or a promoter in *Escherichia coli* capable of expression in acetic acid bacteria. As examples of the promoter in *Escherichia coli*, there may be mentioned the ampicillin-resistant gene in *E. coli* plasmid pBR322, the kanamycin-resistant gene in *E. coli* plasmid pACYC177, the chloramphenicol-resistant gene in *E. coli* plasmid pACYC184 and the promoter for β-galactosidase gene in *E. coli*. If excess ALDH is produced to adversely affect the growth of host cells, a proper promoter must be selected to control the degree of gene expression. Cases are often observed in which a protein having a molecular weight different from that of ALDH is formed. This is a fused protein composed of ALDH and another type of protein, and offers no problem if the enzyme activity of ALDH can be normally expressed.

As the vector to retain the DNA fragment containing the structural gene for ALDH in acetic acid bacteria, may be used, for example, pTA5001(A) and pTA5001(B) disclosed in Japanese Patent Kokai No.9488/1985, as well as vectors wide host range that can be introduced into acetic acid bacteria, such as RP4::Mu, RP4, pRK2013 and RSF1010.

A plasmid containing the structural gene for ALDH can thus be isolated and introduced to the host, whereby ALDH protein can be produced in large quantities inside the cells.

As the host for producing ALDH, may be used strains of *Escherichia coli* and *Bacilus subtilis* for which DNA recombination techniques have been established, but it is more preferable to use acetic acid bacteria which are by nature capable of producing ALDH, such as strains of Acetobacter and Gluconobacter.

ALDH has PQQ as prosthetic group; hence, PQQ may be added to the culture medium for the production of highly active ALDH protein. However, it is more preferable for this purpose to adopt a host capable of producing PQQ. As described in Agricultural and Biological Chemistry, 48, 561 (1984), the capacity of synthesizing PQQ is high with acetic acid bacteria, but is rather low with *Escherichia coli* and *Bacillus subtilis*. Furthermore, recycling between oxidized PQQ and reduced PQQ should proceed smoothly for efficient progress of the enzyme reaction, and the use of an acetic acid bacterium as host is advantageous in this respect, too, because the electrons formed by the reduction reaction become conjugated with the electron transport system to allow efficient recycling.

ALDH participates in the oxidation of acetaldehyde into acetic acid in the acetic acid fermentation process. An increase in the amount of ALDH in the microbial cells would therefore enhance the efficiency of the fermentation process. As is shown in EXAMPLE 3, the higher ALDH activity achieved by the use of a transformant of acetic acid bacterium actually enhances the fermentation efficiency.

EFFECTS ACHIEVED BY THE INVENTION

This invention allows easy preparation of ALDH, an enzyme which was difficult to purify because of the low productivity by microorganisms, thus expanding its use as an enzyme for quantitative analysis and for deodorization. In addition, the efficiency of acetic acid fermentation can be enhanced by the use of an acetic acid bacterium with a higher content of ALDH.

EXAMPLE 1

Preparation of anti-ALDH antibody

*Acetobacter altoacetigenes* MH-24 strain (FERM BP-491) was cultured with shaking at 30° C. in a medium containing 3% glucose, 4% (by volume) ethanol, 6% (by volume) acetic acid, 0.5% yeast extract (Daigo Eiyo-kagaku Co.) and 0.2% polypeptone (Daigo Eiyo-kagaku Co.). The grown cells were collected by centrifugal separation, and 4 mg ALDH complex was isolated from the cells by the usual method disclosed in Japanese Patent Kokai No.12279/1988. This complex was subjected to electrohoresis on SDS-polyacrylamide gel for separation into a protein having a molecular weight of about 75,000 and another protein having a molecular weight of about 20,000, and the former protein was eluted from the gel and isolated as the standard product of ALDH.

ALDH thus obtained (0.1 mg) was subcutaneously injected to a rabbit together with complete Freund's adjuvant, and the same amount was again injected about two weeks later. One month after the first injection, a blood sample was taken from the ear, and the serum was separated from the sample by centrifugation. Precipitation reaction was observed when the serum was tested for reactivity with ALDH. Practically no reactivity was observed with proteins other than ALDH when the cell debris of *Acetobacter altoacetigenes* was subjected to electrophoresis on SDS-polyacrylamide gel and tested for its specificity by the Western blot technique, indicating the formation of anti-ALDH antibody with high specificity.

Isolation of a part of structural gene for ALDH

From the cells of *Acetobacter altoacetigenes* MH-24 strain grown in the same manner as above, was prepared the total DNA by the known method disclosed in Japanese Patent Kokai No.9489/1985). It was cleaved with restriction enzyme PstI (Takara Shuzo Co., Ltd.), and the DNA fragments thus formed were ligated, by the aid of T4 DNA ligase (Takara Shuzo Co., Ltd.), with *E. coli* vector PUC18 (Takara Shuzo Co., Ltd.) previously cleaved with PstI and dephosphorylized with alkaline phosphatase of microbial origin (Takara Shuzo Co., Ltd). The reaction mixture was used for transforming *E. coli* JM 109 strain by the method of Hanahan ["DNA Cloning", Vol. 1, p 109, IRL Press (1985)], and transformants were screened out by culture on LB-agar medium containing 30 μg/ml ampicillin ("A Manual for Genetic Engineering", p201, Cold Spring Harbor Laboratory, 1980). The recombination frequency was about 60%. The transformants thus obtained (about 5,000 strains) were tested for reactivity with anti-ALDH antibody according to the method of Wang et al. [Gene, 37, 267 (1985)] as described below. The transformants grown on the LB medium were replicated on a nitrocellulose filter and incubated at 37° C. for three to five hours, and the colonies grown on the filter were moistened with a 10 mM aqueous solution of IPTG (isopropyl-β-thiogalactopyranoside) to induce the lac promoter of pUC18 so as to cause the host cells (E. coli) to produce fused protein in large quantities. The induction by IPTG was carried out 37° C. for three to five hours, and the filter was exposed to chloroform vapor for ten minutes to pretreat the colonies and then immersed overnight in buffer A (50 mM Tris-HCl, 150 mM NaCl; pH 7.5) further containing 5 mM $MgCl_2$, 5 μg/ml DNase, 0.1 mg/ml lysozyme and 0.5% BSA to completely lyse the colonies, to cause the nitrocellulose filter to adsorb the microbial proteins, and to effect blocking at the same time. The filter was washed three times with buffer A, and immersed at room temperature for five hours in a 1:1000 dilution of anti-ALDH antibody prepared above in buffer A. After washing the filter five times with buffer A, whether the antigen-antibody reaction took place or not was checked as follows. The filter was allowed to react at room temperature for one hour with a 1:2000 dilution of peroxidase-labeled, anti-rabbit IgG antibody (Bio-rad Laboratories) as the secondary antibody, washed three times with buffer A, and immersed in a solution containing hydrogen peroxide and 4-chloro-1-naphthol as color developer. As a result, two of the ampicillin-resistant transformants (about 5,000 strains) turned out to have reacted with the antibody. Extraction of plasmids from these two strains by the alkaline lysing technique [Nucleic Acids Res., 7, 1513 (1979)] and analysis of the extracted plasmids by cleavage with restriction enzymes revealed that both of the strains contain a DNA fragment of about 2.0 Kb at the PstI site of vector pUC18. Separately, the transformant was cultured overnight at 37° C. in LB medium containing 30 μg/ml ampicillin and 10 mM IPTG, the grown cells were disrupted by ultrasonication, the cell debris thus obtained was subjected to electrophoresis on SDS-polyacrylamide gel, and the molecular weight of the protein that reacts with anti-ALDH antibody was determined by the Western blot technique [Anal. Biochem. 112, 195 (1981)]. As a result, it was found that a protein having a molecular weight of about 40,000 reacted with the antibody. This indicates that, since the molecular weight of ALDH is 75,000, the gene isolated above is a gene that codes for about half of the ALDH protein.

Figure 1:
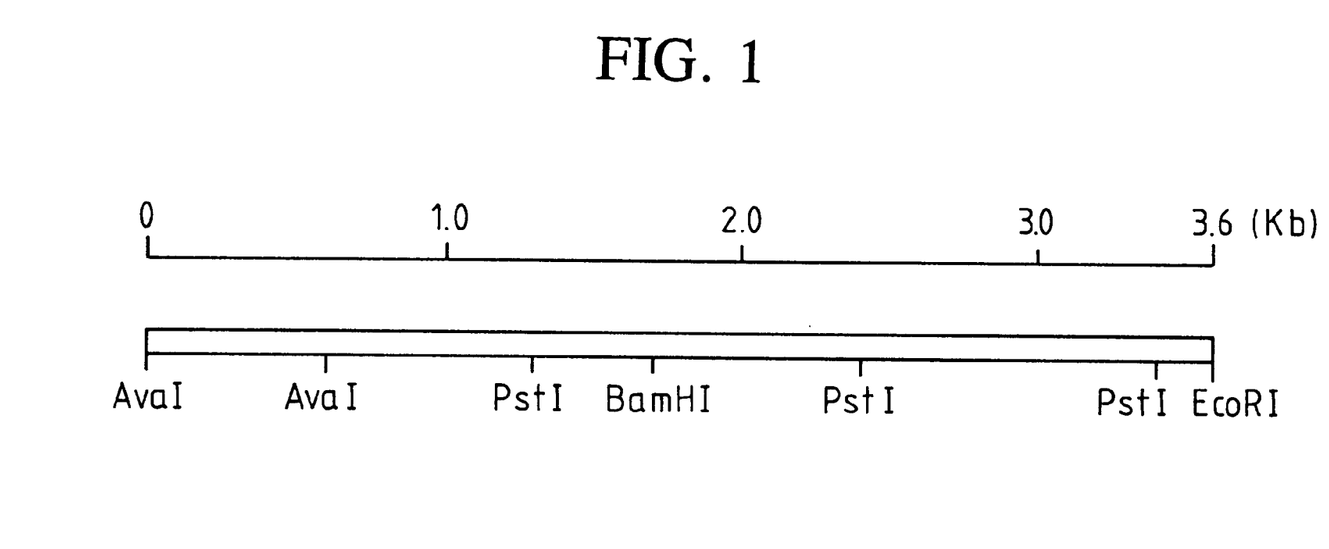
FIG. 1 is a restriction enzyme cleavage map for the DNA fragment containing structural gene for the membrane-bound aldehyde dehydrogenase.

Isolation of DNA fragment containing the total length of the structural gene for ALDH A DNA fragment containing the total length of the structural gene for ALDH was isolated as described below according to the Southern hybridization technique [J. Mol. Biol. 98, 503 (1975)] using, as probe, the gene obtained above (about 2.0 Kb in size) containing a part of that structural gene. The total DNA of Acetobacter altoaceti- genes MH-24 was prepared as stated above, and subjected to partial decomposition by the use of restriction enzyme BamHI under such conditions that the sizes of resulting fragments will be mainly 20 to 30 Kb. The fragments thus formed were ligated, by the aid of T4 DNA ligase, with E. coli cosmid vecter pHC79 [Gene, 11, 291 (1980)] previously cleaved with BamHI, and the ligated product was subjected to packaging by using the in-vitro packaging kit (Promega- biotech Co.). Separately, E. coli HB101 strain (host) was cultured overnight at 30° C. in LB medium containing 0.2% maltose, and the grown cells were collected by centrifugation and suspended in LB medium containing 10 mM $MgCl_2$. To this suspension, was added 0.5 ml of the packaged product obtained above, the mixture was gently stirred and allowed to stand at room temperature for 20 minutes, 4 ml of LB medium was then added, and shake culture was continued at 37° C. for one hour. The culture solution thus obtained was plated on LB-agar medium containing 30 μg/ml ampicillin and incubated overnight at 37° C., and about 1000 strains of the transformants developed were tested for the presence of a plasmid capable of hybridization with a probe by the Southern hybridization technique. Three strains of the transformants tested proved to contain a DNA capable of hybridization with the probe, and one of them was used for cloning of a DNA fragment containing the total length of the structural gene for ALDH. Based on the fact (revealed by the Southern hybridization) that the probe DNA was contained in an about 10 Kb fragment cleaved by EcoRI, this fragment was first isolated as pUC18 vector. This fragment was then subjected to partial decomposition by the use of AvaI, and a fragment containing the total length of ALDH structural gene was isolated. It has a molecular size of about 3.6 Kb and a restriction enzyme map as shown in FIG. 1. This gene fragment was spliced to E. coli vector pUC18 at the EcoRI-AvaI site in such a direction that the control by lac promoter will work, and the transformant thus created was deposited to FRI under the name of E. coli AL25 (FERM BP-2288 (FERM P-9911)). This transformant was cultured overnight at 37° C. in LB medium containing 30 μg/ml ampicillin and 10 mM IPTG, and the grown cells were analyzed by the Western blot technique. The result was that a protein specifically reactive with anti-ALDH antibody and having a molecular weight of about 79,000 had been produced in a significant quantity. No such protein was produced in the absence of IPTG, indicating that ALDH protein was produced under the control of lac promoter in this transformant. The larger molecular weight of the produced protein than that of the original ALDH is probably because it was produced in the form of a fused protein with a different protein derived from the gene just behind lac promoter. The ALDH enzyme activity of the E. coli transformant was measured according to the method used for acetic acid bacteria [Agricultural and Biological Chemistry, 4, 503 (1980)], but no activity was detected.

EXAMPLE 2

Transformation of an acetic acid bacterium with the DNA fragment containing the structural gene for ALDH The DNA fragment isolated in EXAMPLE 1 containing the ALDH structural gene as shown in FIG. 1 was spliced to pCU18 at its AvaI site in such a direction as to allow synthesis of ALDH protein, the resulting recombinant plasmid was cleaved with restriction enzyme SalI, and cut ends were made flush by the aid of T4 DNA polymerase. Separately, a plasmid having a molecular size of about 2.1 Kb in Acetobacter aceti subspecies xylinum IFO 3288 was isolated and cleaved with restriction enzyme AccI, and the cut ends were made flush by the aid of T4DNA polymerase. The two types of cleaved DNA fragments obtained above were ligated together by the use of T4 DNA ligase, and the resulting recombinant DNA was used to transform, according to the method described in Agricultural and Biological Chemistry, 49, 2091 (1985), a mutant strain 10-812 with lowered ALDH activity derived from Acetobacter aceti No.1023 (FERM BP-2287 (FERM P-7122)) by the method disclosed in Agricultural and Biological Chemistry, 49, 2485 (1985). The transformants thus obtained were incubated on YPG-agar medium (3% glucose, 0.5% yeast extract, 0.2% polypeptone and 2% agar; pH 6.5) further containing 50 μg/ml ampicillin, and the plasmids in the ampicillin-resistant strain grown on that medium were examined according to the method described in Agricultural and Biological Chemistry, 49, 2083 (1985). Molecular size of the introduced plasmid was found to be about 8.3 Kb. Analysis by the action of restriction enzymes revealed that this plasmid is a chimera plasmid composed of three fragments: pUC18, the gene fragment shown in FIG. 1, and an about 2.1 Kb plasmid of Acetobacter aceti subspecies xylinum (IFO3288).

Properties of the transformant of Acetobacter

The transformant of Acetobacter aceti obtained above was tested for the amount of ALDH protein formed by the Western blot technique. It was cultured with shaking in YPG liquid medium (YPG-agar medium from which agar has been eliminated) containing 30 μg/ml amipicillin at 30° C. for 36 hours, and the grown cells were collected and suspended in McIlvaine buffer (pH 6.0) and disrupted by means of a French press. After removing undisrupted microbial cells by centrifugation (5,000 rpm, 10 minutes), the supernatant was subjected to electrophoresis on SDS-polyacrylamide gel, and the formation of proteins that react specifically with anti-ALDH antibody was examined by the Western blot technique. It was demonstrated that a protein having a molecular weight of about 79,000 had actively reacted with the antibody. On the other hand, no such protein was formed in the parent strain. The ALDH enzyme activity of the transformant was measured by the method described in EXAMPLE 1. Its specific activity was 0.43 as against 0.15 with the parent strain—an about three-fold increase in activity. The larger molecular weight of that protein reactive with anti-ALDH antibody than that of the original ALDH is probably because it was produced in the form of a fused protein as in the case with E. coli described in EXAMPLE 1. This offers no practical problem because the produced protein shows normal enzyme activity even with the larger molecular weight. As is apparent from the foregoing, the intracellular ALDH content of acetic acid bacteria can be increased by transformation with a recombinant DNA containing the structural gene for ALDH.

EXAMPLE 3

Acetic acid fermentation using a transformant of Acetobacter

Figure 2:
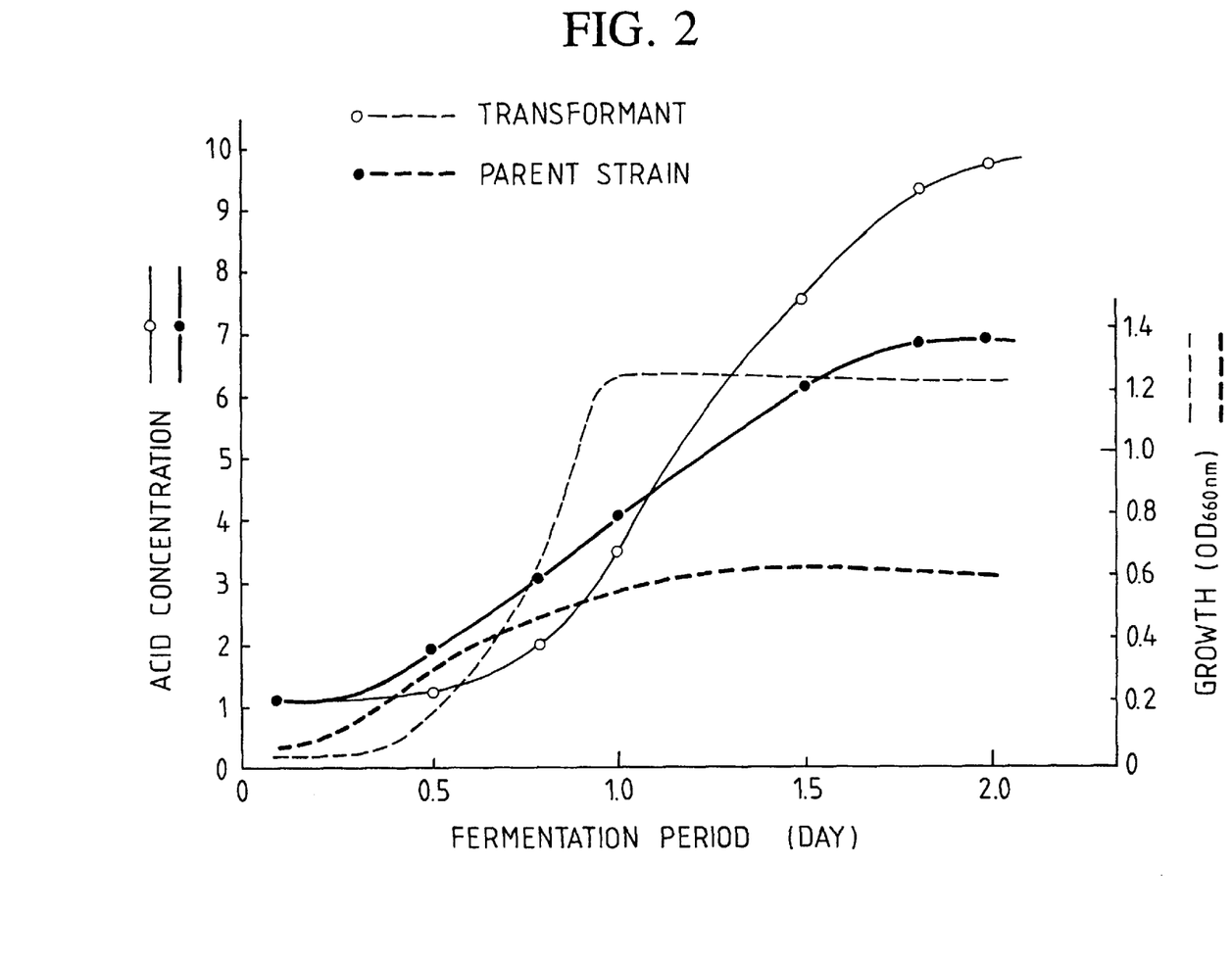
FIG. 2 is a graph comparing the efficiency of acetic acid fermentation caused by the parent strain and by the transformant described in EXAMPLE 3.
Figure 3A:
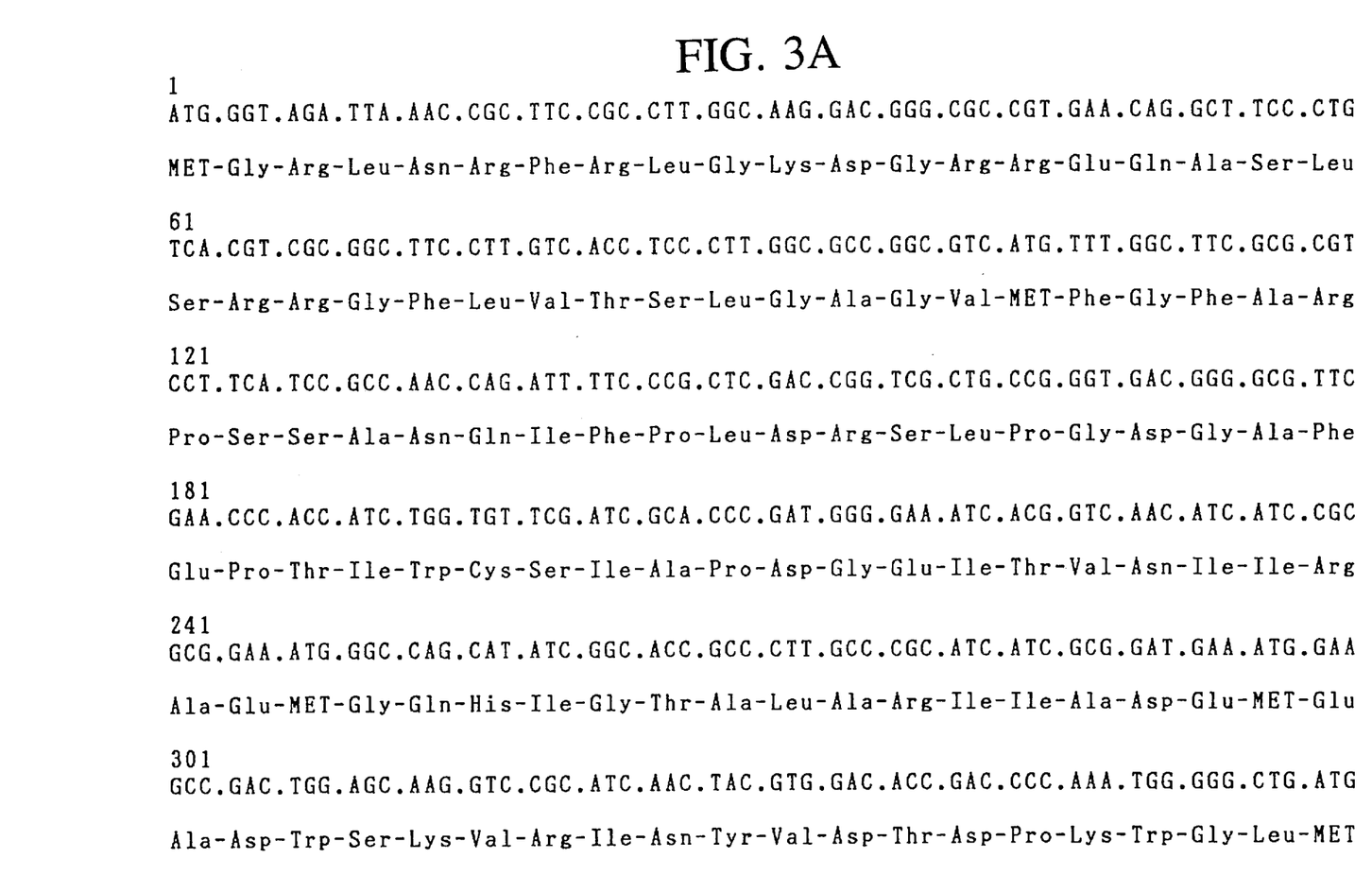
FIG. 3 shows the base sequence of the structural gene for the membrane-bound aldehyde dehydrogenase (upper rows) and the amino acid sequence of the same (lower rows).
Figure 3B:
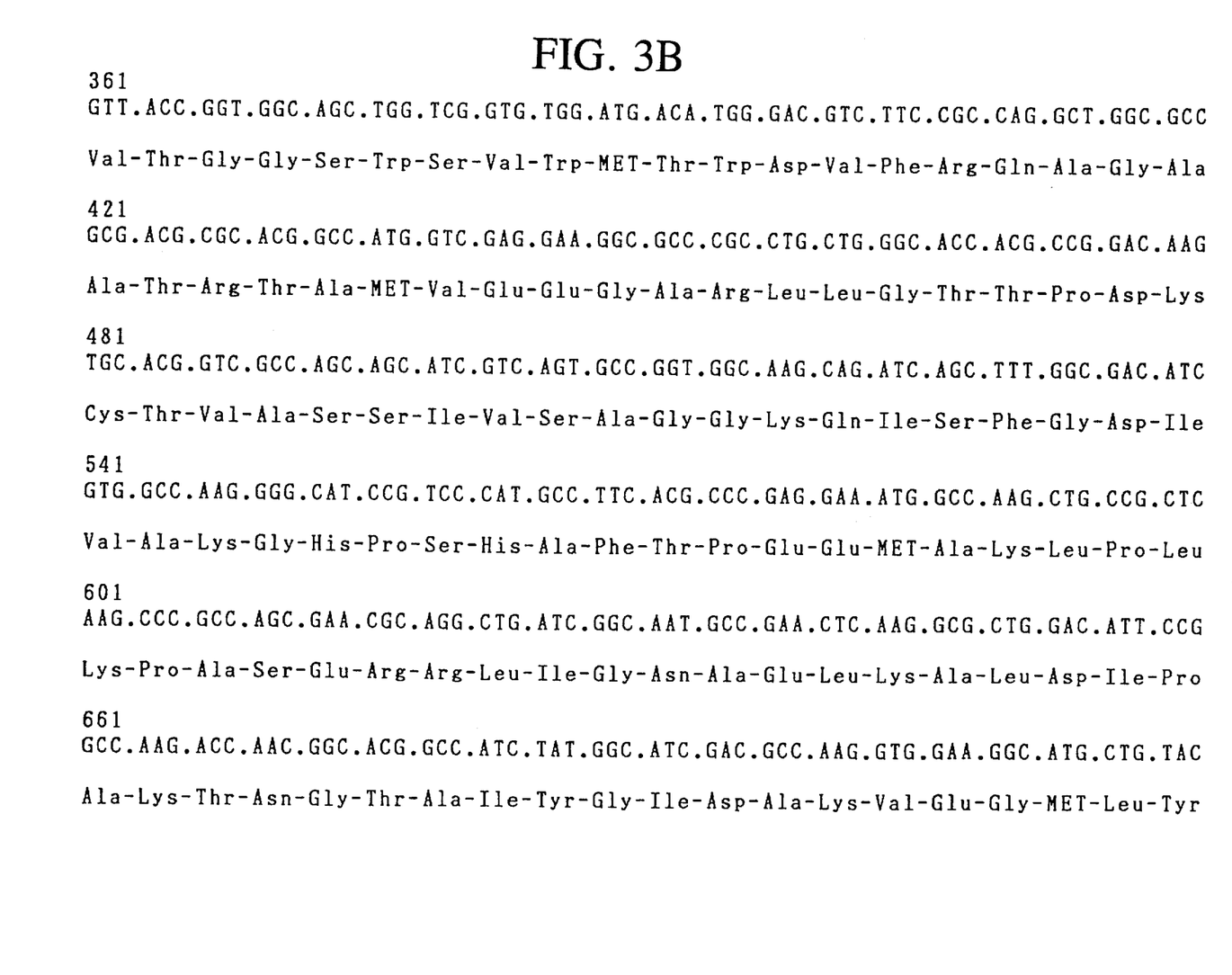
Figure 3C:
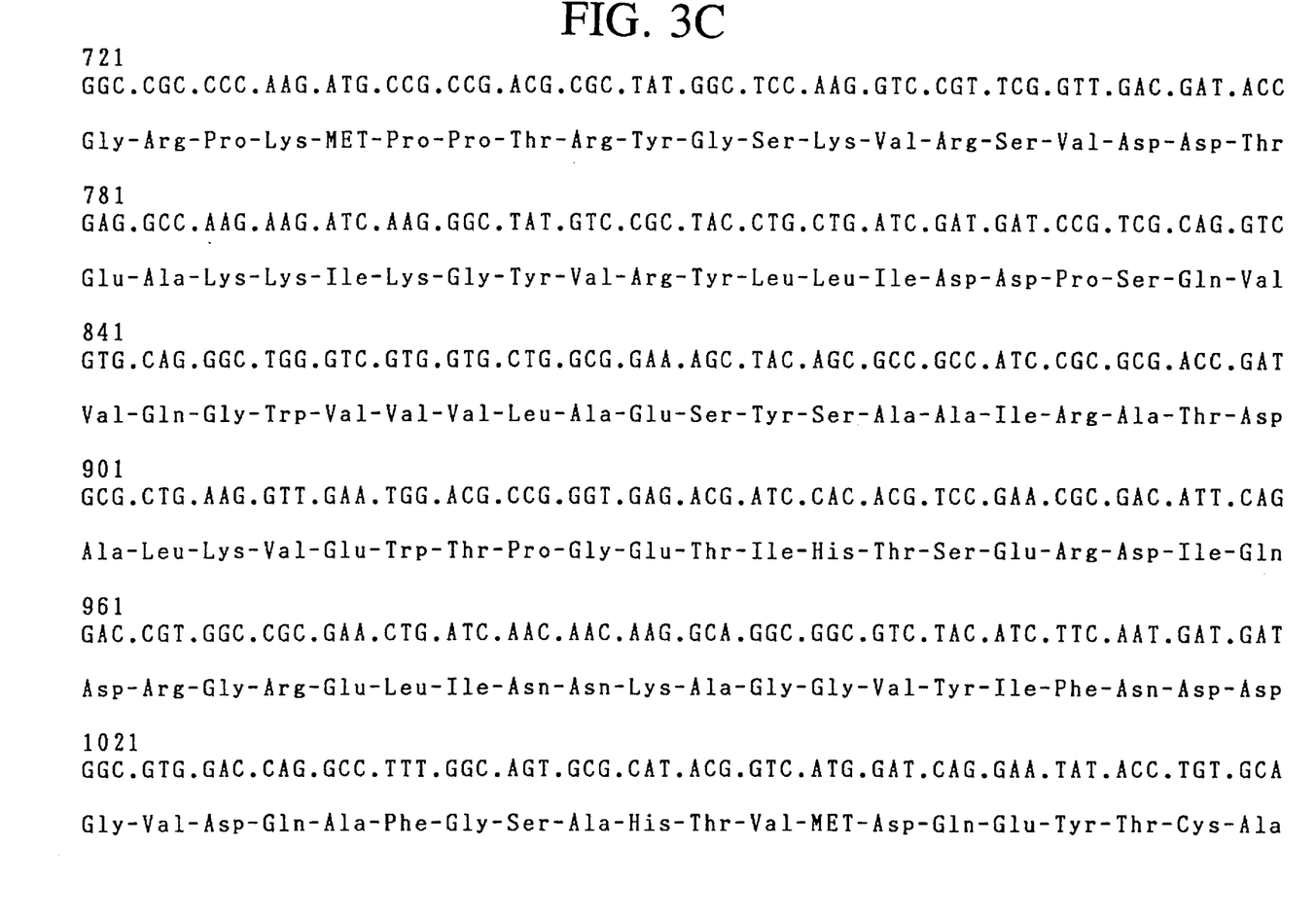
Figure 3D:
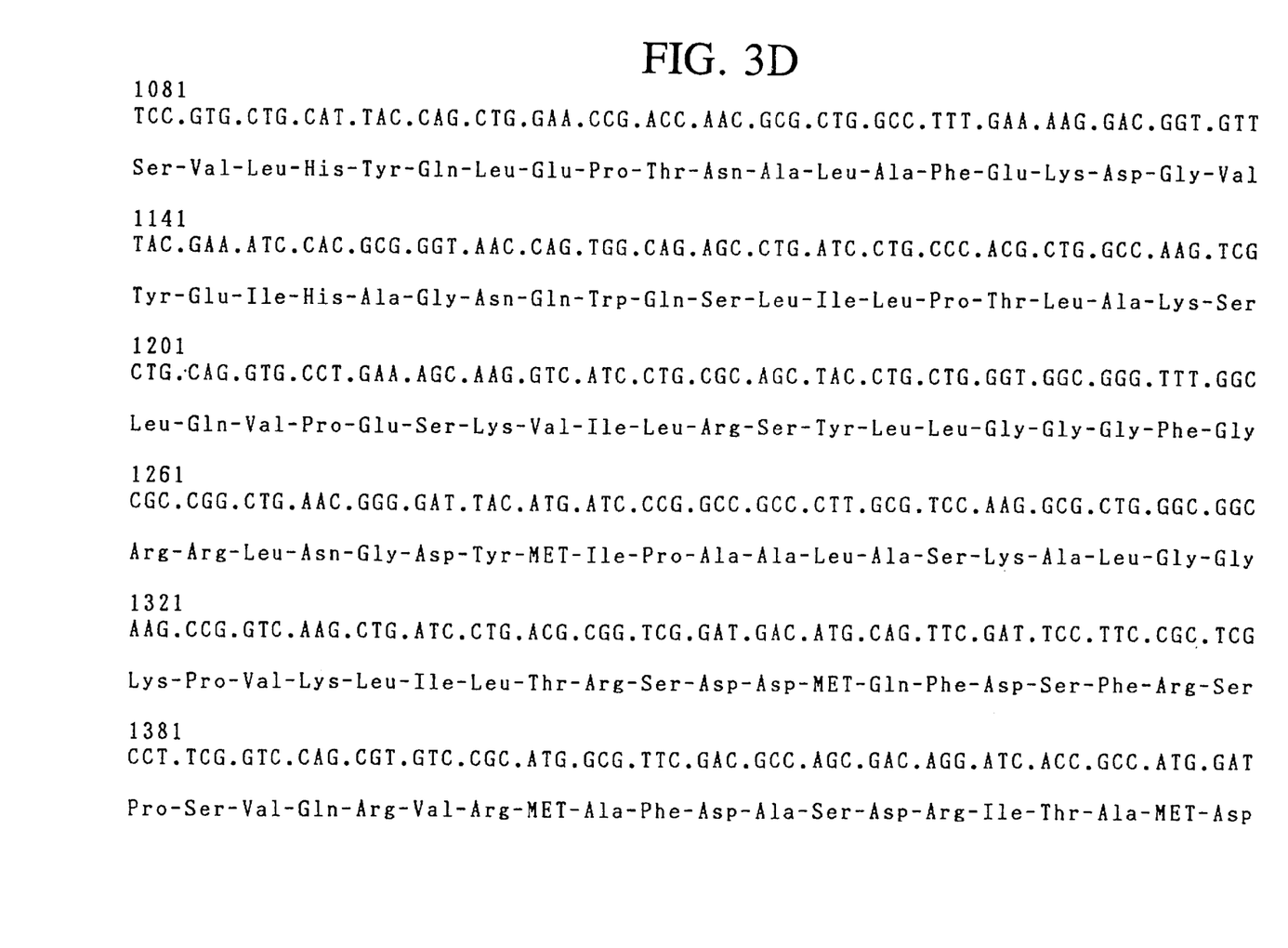
Figure 3E:
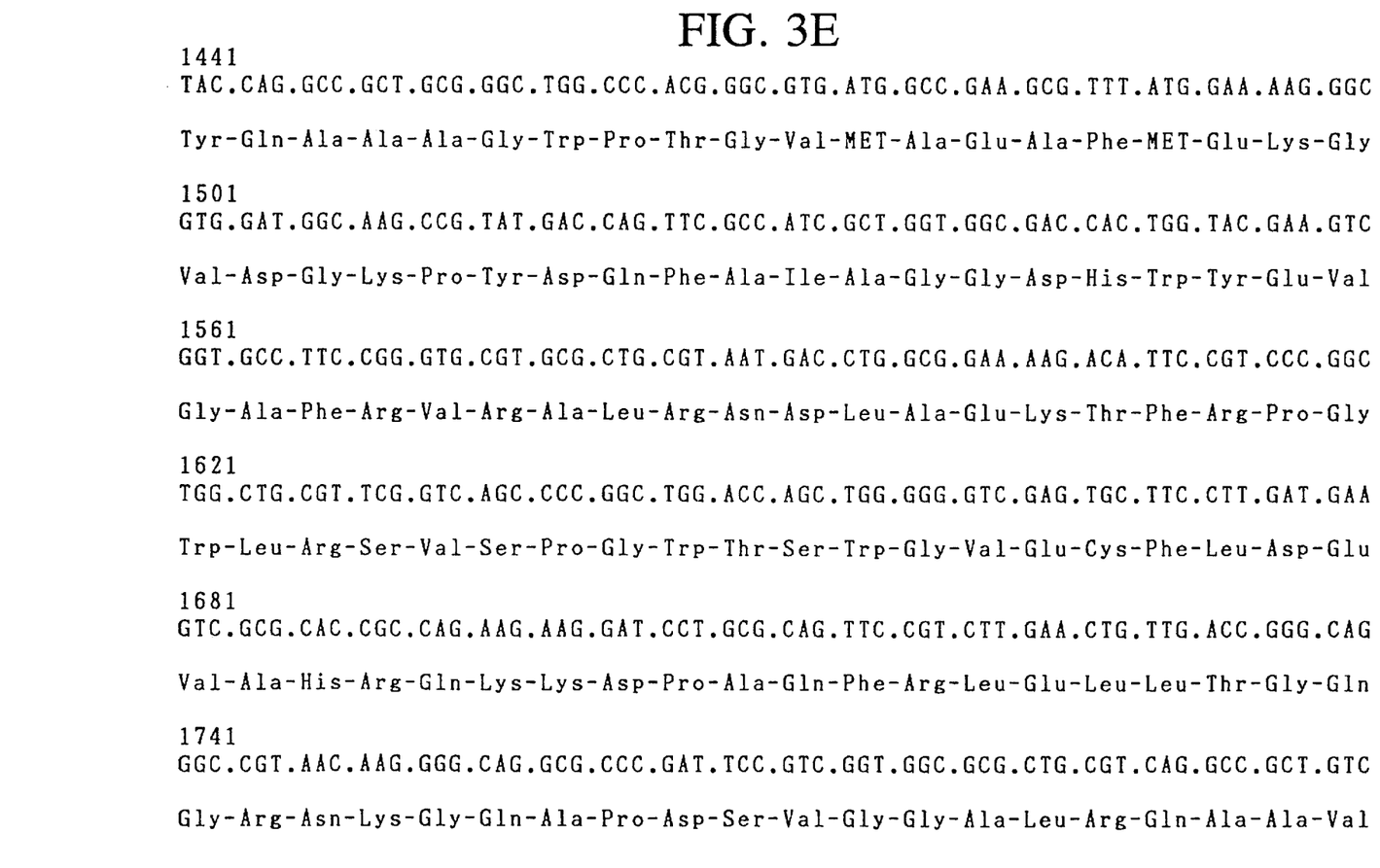
Figure 3F:
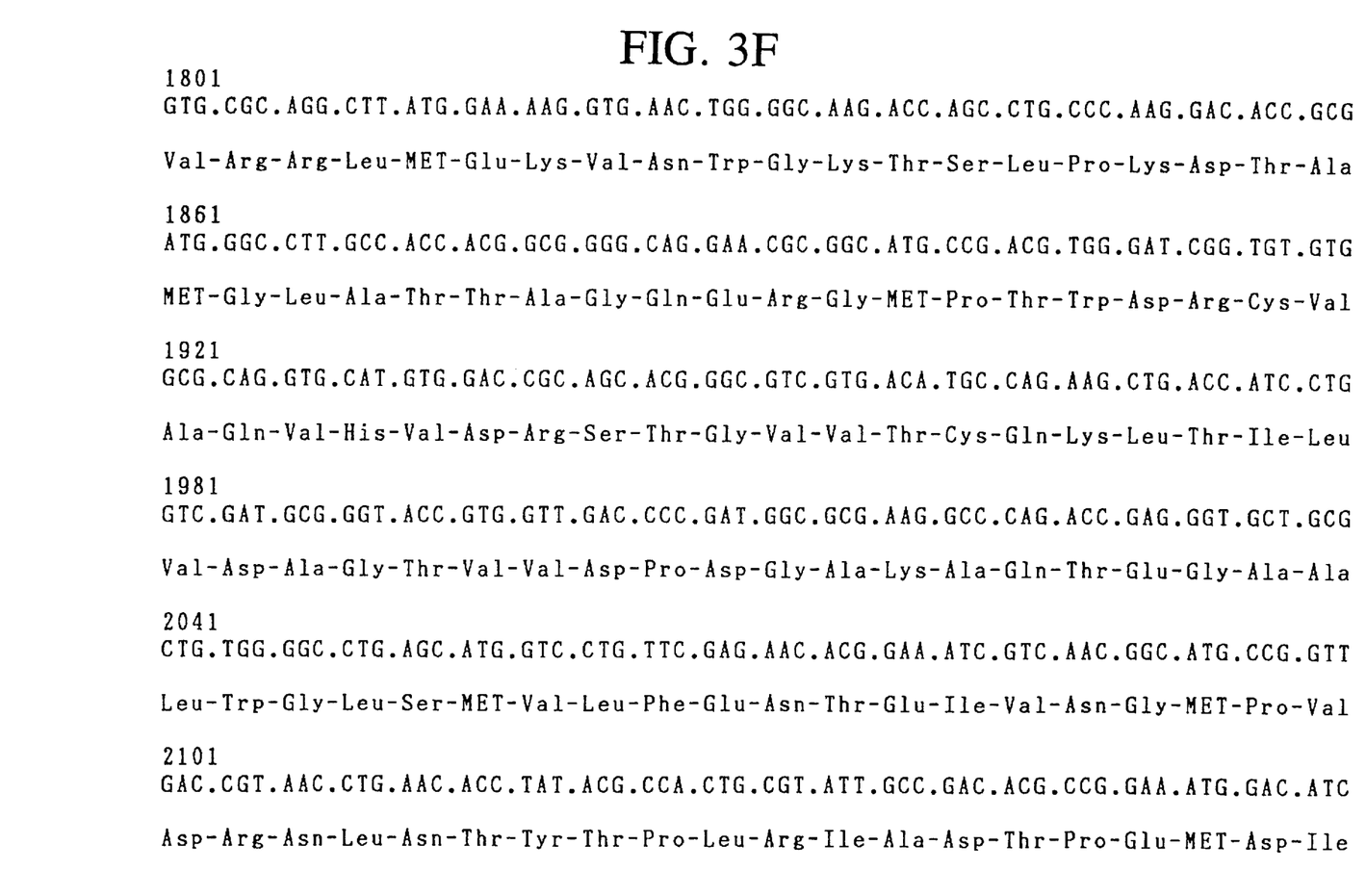
Figure 3G:
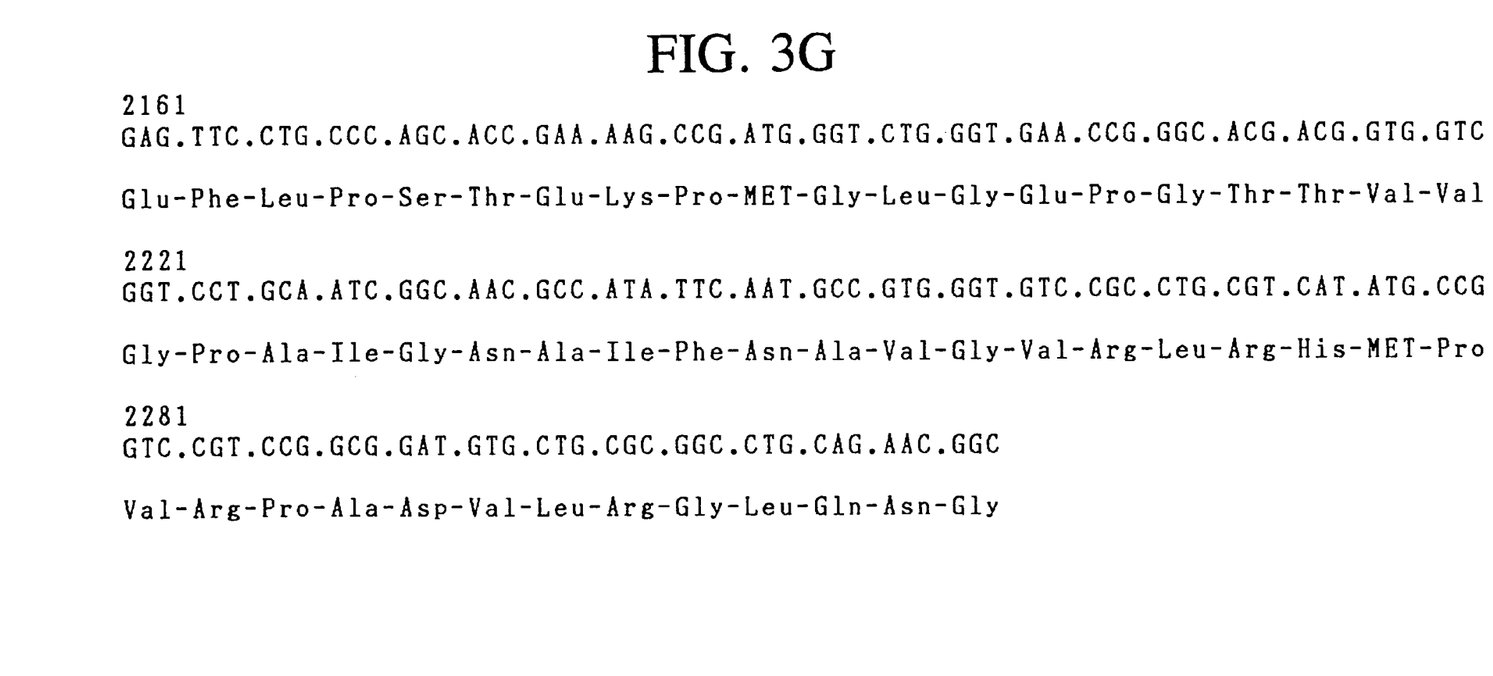

Acetobacter aceti subspecies xylinum IFO3288 was transformed by introducing a chimera plasmid composed of three components (the DNA fragment containing the ALDH structural gene obtained in EXAMPLE 2, E. coli plasmid pUC18, and acetic acid bacterium plasmid) according to the method described in Agricultural and Biological Chemistry, 49, 2091 (1985). The intended transformant was screened out by culture on YPG-agar medium containing 500 μg/ml ampicillin, and plasmids in the ampicillin-resistant strain grown on this selective medium were analyzed by the same method as in EXAMPLE 2. It was confirmed that the transformant contains the chimera plasmid of about 8.3 Kb in size. The transformant containing this chimera plasmid was compared with the parent strain not containing the same for acetic acid fermentation capacity. FIG. 2 shows the course of fermentation conducted in a 5-liter minijar.

YPG-agar medium used in EXAMPLE 2 further containing suitable amounts of ethanol and acetic acid was employed as the fermentation medium, which was charged in the jar in an amount of three liters. Fermentation was carried out at 30° C. with agitation (500 rpm) and aeration (0.2 vvm). Table 1 shows the data on the relative growth rate of microbial cells, the rate of acetic acid formation for unit volume, and the final acid concentration. As can be seen from the table, the transformant is far better than the parent strain in all of these items. A test on continuous fermentation at an acid concentration of 4% showed that a steady state was reached at a feed rate of 150 ml/hr with the parent strain, while continuous fermentation could be carried on up to a feed rate of 250 ml/hr with the transformant.

TABLE 1

|  | Parent Strain | Transformant |
| --- | --- | --- |
| Relative growth rate (1) ( /hr) | 0.072 | 0.143 |
| Acid formation rate (2) (%/hr) | 0.18 | 0.40 |
| Final acid concentration (%) | 6.84 | 9.66 |

(1): at 3% acid concentration
(2): at 2% acid concentration

EXAMPLE 4

Determination of the base and amino acid sequences of the structural gene for the membrane-bound aldehyde dehydrogenase The transformant, E. coli AL25, obtained in EXAMPLE 1 was treated by the alkaline lysing technique, and the plasmid thus extracted was cleaved with EcoRI, isolating a DNA fragment of about 3.6 Kb having a restriction enzyme cleavage map as shown in FIG. 1. Its base sequence was determined by the dideoxy method using M13 phage ("Methods in Enzymology", 10, 20, 1983, Academic Press, New York). From this base sequence, was found a translation region starting with the initiation codon, ATG, and consisting of 2349 bases which code for 773 amino acids (total molecular weight: 84,135) as shown in FIG. 3. The amino acid sequence determined from the above base sequence is shown in the lower rows in FIG. 3). The identity of the polypeptide shown by the base sequence in FIG. 3 with the membrane-bound aldehyde dehydrogenase of this invention was proved by the fact that the ten amino acid sequence on the side of amino terminal (Asn-Gln-Ile-Phe-Pro-Leu-Asp-Arg-Ser-Leu) determined by the Edman degradation of purified ALDH is in complete agreement with the amino acid sequence from the 45th acid on the side of amino terminal shown in FIG. 3. The amino acid sequence up to the 44th acid, found in the sequence determined by the Edman degradation, is considered to be a region participating in the secretion of the membrane-bound aldehyde dehydrogenase.

What is claimed is:

1. An isolated structural gene for a membrane-bound aldehyde dehydrogenase, which has the base sequence as shown in FIG. 3.

2. An isolated structural gene for a membrane-bound aldehyde dehydrogenase, which codes for the amino acid sequence as shown in FIG. 3.

3. An isolated structural gene for the membrane-bound aldehyde dehydrogenase derived from microorganisms belonging to the genus Acetobacter, said isolated structural gene having a cleavage map as shown in FIG. 1.

4. An isolated structural gene for membrane-bound aldehyde dehydrogenase according to claim 1, which is derived from microorganisms belonging to the genus Acetobacter.

5. An isolated structural gene for membrane-bound aldehyde dehydrogenase according to claim 2 which is derived from microorganisms belonging to the genus Acetobacter.

6. An isolated DNA consisting essentially of a sequence of DNA bases coding for the amino acid sequence for membrane-bound aldehyde dehydrogenase shown in FIG. 3.

7. An isolated DNA consisting essentially of the sequence of DNA bases shown in FIG. 3.

8. A plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said isolated structural gene having a molecular size of about 3.6 kb, and having a restriction enzyme cleavage map as shown in FIG. 1, said promoter being a promoter for β-galactosidase of *Escherichia coli*.

9. Acetic acid bacteria transformed by a plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said isolated structural gene having a molecular size of about 3.6 kb and having a restriction enzyme cleavage map as shown in FIG. 1, said promoter being a promoter for β-galactosidase of *Escherichia coli*.

10. In the method of acetic acid fermentation, the improvement comprising using a strain belonging to the genus Acetobacter or Gluconobacter transformed by a plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said purified structural gene having a molecular size of about 3.6 kb and having a restriction enzyme cleavage map as shown in FIG. 1, said promoter being a promoter for β-galactosidase of *Escherichia coli*.

11. A plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said isolated structural gene having a molecular size of about 3.6 kb, and having a base sequence as shown in FIG. 3, said promoter being a promoter for β-galactosidase of *Escherichia coli*.

12. Acetic acid bacteria transformed by a plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said isolated structural gene having a molecular size of about 3.6 kb and having a base sequence as shown in FIG. 3, said promoter being a promoter for β-galactosidase of *Escherichia coli*.

13. In the method of acetic acid fermentation, the improvement comprising using a strain belonging to the genus Acetobacter or Gluconobacter transformed by a plasmid for expression of membrane-bound aldehyde dehydrogenase derived from microorganisms belonging to the genus Acetobacter, said plasmid containing the isolated structural gene for membrane-bound aldehyde dehydrogenase derived from microorganisms belonging to the genus Acetobacter and a promoter therefor, said purified structural gene having a molecular size of about 3.6 kb and having a base sequence as shown in FIG. 3, said promoter being a promoter for β-galactosidase of *Escherichia coli*.

* * * * *